United States Patent
Alsheikh et al.

(10) Patent No.: US 11,202,736 B2
(45) Date of Patent: Dec. 21, 2021

(54) ANTIMICROBIAL DENTAL RESTORATIVES CONTAINING COCONUT OIL AND/OR DERIVATIVES OF COCONUT OIL

(71) Applicant: Imam Abdulrahman Bin Faisal University, Dammam (SA)

(72) Inventors: Rasha Numan Ali Alsheikh, Alkhobar (SA); Naif Nasser Almasoud, Alkhobar (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 726 days.

(21) Appl. No.: 15/897,724

(22) Filed: Feb. 15, 2018

(65) Prior Publication Data

US 2019/0247282 A1 Aug. 15, 2019

(51) Int. Cl.
| | |
|---|---|
| *A61K 6/69* | (2020.01) |
| *A61K 9/00* | (2006.01) |
| *A61K 36/889* | (2006.01) |
| *A61K 31/20* | (2006.01) |
| *A61K 31/201* | (2006.01) |
| *A61K 6/60* | (2020.01) |
| *A61K 6/62* | (2020.01) |
| *A61K 6/71* | (2020.01) |
| *A61K 6/76* | (2020.01) |
| *A61K 6/77* | (2020.01) |
| *A61K 6/887* | (2020.01) |

(52) U.S. Cl.
CPC ............ *A61K 6/69* (2020.01); *A61K 6/60* (2020.01); *A61K 6/62* (2020.01); *A61K 6/71* (2020.01); *A61K 6/76* (2020.01); *A61K 6/77* (2020.01); *A61K 6/887* (2020.01); *A61K 9/0053* (2013.01); *A61K 31/20* (2013.01); *A61K 31/201* (2013.01); *A61K 36/889* (2013.01)

(58) Field of Classification Search
None
See application file for complete search history.

(56) References Cited

U.S. PATENT DOCUMENTS

| | | | |
|---|---|---|---|
| 4,256,730 A | 3/1981 | Benedict | |
| 7,850,453 B2 | 12/2010 | Jodaikin et al. | |
| 8,703,897 B2 | 4/2014 | Gan et al. | |

FOREIGN PATENT DOCUMENTS

| | | |
|---|---|---|
| CN | 101180099 B | 2/2013 |
| CN | 102099004 B | 8/2014 |
| CN | 105596260 A | 5/2016 |
| EP | 0 604 158 A1 | 6/1994 |

OTHER PUBLICATIONS

Wille, et al., Dental Materials, 32:1073. (Year: 2016).*
Tosoh, Zirconia Brochure, Tosoh Yttria-stabilized Zirconia (YSZ). (Year: 2016).*
Peedikayil, et al., Journal of International Society of Preventive and Community Dentistry, 6:447. (Year: 2016).*
Natural Brite, "Virgin Coconut Oil Toothpaste", Shopee.com, URL: https://shopee.com.my/Virgin-Coconut-Oil-Toothpaste-i.4367157.150509955, 2 Pages total, (Nov. 23, 2017).
Chaudhari, S., et al., "Comparison between Homemade Toothpaste and Commercial Tooth Paste in Plaque Removal of Children's in Udaipur City Rajasthan", IOSR Journal of Dental and Medical Sciences (IOSR-JDMS), vol. 16, Issue 5, pp. 91-93, (May 2017).
Liao, W., et al., "The Interaction of Various Liquids with Long-Term Denture Soft Lining Materials", Dental Materials, URL: http://www.sciencedirect.com/science/article/pii/S010956411200142X, vol. 28, Issue 10, 1 Page total, (Oct. 2012) (Abstract only).

* cited by examiner

*Primary Examiner* — Michael Barker
(74) *Attorney, Agent, or Firm* — Oblon, McClelland, Maier & Neustadt, L.L.P.

(57) ABSTRACT

A dental restorative based on a cured dental composite containing coconut oil and/or a derivative of coconut oil. The dental restorative also includes a polymerizable monomer, a filler, and a polymerization initiator. Methods of preventing or reducing growth of microorganisms and inhibiting formation of biofilms are also described.

13 Claims, No Drawings

ANTIMICROBIAL DENTAL RESTORATIVES CONTAINING COCONUT OIL AND/OR DERIVATIVES OF COCONUT OIL

BACKGROUND OF THE INVENTION

Technical Field

The present disclosure relates to a dental composite and dental restorations thereof comprising coconut oil and/or a derivative of coconut oil with antimicrobial properties, together with methods for preventing microbial growth and biofilm formation on a surface in an oral cavity with the dental composite.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Dental caries and gingivitis are two of the most commonly diagnosed microbial infections in oral environments. Gingivitis is an inflammation of the gum caused by a bacterial disorder that affects gingival tissue, the underlying bones, and periodontal ligaments, which can eventually lead to tooth mobility and loss if not treated. Another highly prevalent disease, dental caries is also caused by pathogenic microbes. (Marcenes W, Kassebaum N J, Bernabe E, Flaxman A, Naghavi M, Lopez A et al. (2013). Global burden of oral conditions in 1990-2010: a systematic analysis. *Journal of dental research* 92(7):592-597.) Regular treatments performed in dental clinics include caries management and cavity restoration.

Resin composites have been increasingly used for dental restorations because they meet the growing aesthetic demands from patients. Despite significant improvement in composite formulation and curing conditions, several issues regarding the clinical performance of resin composites remain, such as biofilm accumulation in the tooth/restoration interface, secondary caries formation, and restoration fracture/failure (Moura F R, Romano A R, Lund R G, Piva E, Rodrigues Junior S A, Demarco F F (2011). Three-year clinical performance of composite restorations placed by undergraduate dental students. *Brazilian dental journal* 22(2):111-116; da Veiga A M, Cunha A C, Ferreira D M, da Silva Fidalgo T K, Chianca T K, Reis K R et al. (2016). Longevity of direct and indirect resin composite restorations in permanent posterior teeth: A systematic review and meta-analysis. *Journal of dentistry* 54:1-12; and Alhareky M, Tavares M (2016). Amalgam vs composite restoration, survival, and secondary caries. *The journal of evidence-based dental practice* 16(2):107-109, each incorporated herein by reference in their entirety). Studies have reported that resin composite restorations have a greater tendency to accumulate bacteria, biofilm and plaque compared to other restorative materials, which may be explained by gaps forming in the tooth/restoration interface as a result of polymerization shrinkage, internal stresses and/or material degradation (Beyth N, Domb A J, Weiss E I (2007). An in vitro quantitative antibacterial analysis of amalgam and composite resins. *Journal of dentistry* 35(3):201-206; and Li F, Weir M D, Chen J, Xu H H (2014). Effect of charge density of bonding agent containing a new quaternary ammonium methacrylate on antibacterial and bonding properties. *Dental materials: official publication of the Academy of Dental Materials* 30(4):433-441, each incorporated herein by reference in their entirety). Furthermore, biofilm bacteria release acids as metabolic byproducts, which can demineralize tooth structure and lead to cavities and caries development. Therefore, the presence of biofilm increases the chance of secondary caries and further degradation of placed composite restorations.

Recently, dental resin composites incorporating an antibacterial component have been developed in an attempt to reduce biofilm formation at the tooth/restoration interface and inflammation in gingival tissue, and thus improve service-life of the restoration and oral hygiene of the patient (Altmann A S, Collares F M, Leitune V C, Samuel S M (2016). The effect of antimicrobial agents on bond strength of orthodontic adhesives: a meta-analysis of in vitro studies. *Orthodontics & craniofacial research* 19(1):1-9; and Sharma S, Tandon P, Nagar A, Singh G P, Singh A, Chugh V K (2014). A comparison of shear bond strength of orthodontic brackets bonded with four different orthodontic adhesives. *Journal of orthodontic science* 3(2):29-33, each incorporated herein by reference in their entirety). However, there is a need for a more effective dental restorative that provides good durability and antimicrobial activities.

In view of the forgoing, one objective of the present disclosure is to provide a dental restorative that contains coconut oil and/or a derivative of coconut oil. Another objective of the present disclosure is to provide methods of preventing or reducing growth of a microorganism and inhibiting formation of biofilm in an oral cavity using the dental restorative described herein.

BRIEF SUMMARY OF THE INVENTION

According to a first aspect, the present disclosure relates to a dental composite, comprising (i) a polymerizable monomer, (ii) a filler in an amount of 40-75 wt %, (iii) a polymerization initiator, and (iv) coconut oil and/or a derivative of coconut oil in an amount ranging from 0.1 wt % to 20 wt %, wherein the weight percentages are based on a total weight of the dental composite.

In one embodiment, the derivative of coconut oil is present, and is at least one selected from the group consisting of lauric acid, caprylic acid, capric acid, myristic acid, oleic acid, esters thereof, and salts thereof.

In one embodiment, the derivative of coconut oil is lauric acid, an ester thereof, or a salt thereof.

In one embodiment, the dental composite consists essentially of (i) the polymerizable monomer, (ii) the filler in an amount of 40-75 wt %, (iii) the polymerization initiator, and (iv) coconut oil in an amount ranging from 0.1 wt % to 20 wt %, wherein the weight percentages are based on a total weight of the dental composite.

In one embodiment, the polymerizable monomer is at least one selected from the group consisting of a methacrylate monomer, an acrylate monomer, an epoxy monomer, and a vinyl monomer.

In one embodiment, the polymerizable monomer is a methacrylate monomer.

In one embodiment, the methacrylate monomer is one or more selected from the group consisting of bisphenol A-glycidyl methacrylate (bis-GMA), urethane dimethacrylate (UDMA), triethylene glycol dimethacrylate (TEGDMA), ethoxylated bisphenol A dimethacrylate (EBPADMA), and 2-hydroxyethyl methacrylate (HEMA).

In one embodiment, the filler is at least one selected from the group consisting of a glass filler, a ceramic filler, and a polymer-based filler.

In one embodiment, the filler is at least one selected from the group consisting of silica, zirconia, and aluminosilicate.

In one embodiment, the polymerization initiator is a free radical initiator.

In one embodiment, the free radical initiator is one or more selected from the group consisting of camphorquinone, an acyl phosphine oxide, an azo compound, and an organic peroxide.

According to a second aspect, the present disclosure relates to a dental restoration, comprising a cured dental composite of the first aspect.

In one embodiment, the dental restoration has a flexural strength of about 70 MPa to about 150 MPa.

In one embodiment, the dental restoration has a Vickers hardness number HV of about 60 to about 100.

According to a third aspect, the present disclosure relates a method of preventing or reducing growth of a microorganism in an oral cavity, the method comprising applying the dental restoration of the second aspect to the oral cavity of a subject in need thereof.

In one embodiment, the microorganism is at least one selected from the group consisting of *Streptococcus mutans* and *Streptococcus sobrinus*.

In one embodiment, preventing or reducing growth of the microorganism in the oral cavity is evaluated by measuring a microbial count.

According to a forth aspect, the present disclosure relates a method of inhibiting formation of a biofilm on a surface in an oral cavity, the method comprising applying the dental restoration of the second aspect to a surface in the oral cavity of a subject in need thereof.

In one embodiment, the biofilm comprises at least one selected from the group consisting of *Streptococcus mutans* and *Streptococcus sobrinus*.

In one embodiment, the surface is a tooth surface.

The foregoing paragraphs have been provided by way of general introduction, and are not intended to limit the scope of the following claims. The described embodiments, together with further advantages, will be best understood by reference to the following detailed description.

DETAILED DESCRIPTION OF THE EMBODIMENTS

Unless otherwise specified, "a," "an," "at least one," and "one or more" are used interchangeably.

Within the description of this disclosure, where a numerical limit or range is stated, the endpoints are included unless stated otherwise. Also, all values and subranges within a numerical limit or range are specifically included as if explicitly written out.

As used herein, the term "compound" refers to a chemical entity, whether in a solid, liquid or gaseous phase, and whether in a crude mixture or purified and isolated.

According to a first aspect, the present disclosure relates to a dental composite, comprising (i) a polymerizable monomer, (ii) a filler in an amount of 40-75 wt %, (iii) a polymerization initiator, and (iv) coconut oil and/or a derivative of coconut oil in an amount ranging from 0.1 wt % to 20 wt %, wherein the weight percentages are based on a total weight of the dental composite.

As used herein, a "composite" refers to a combination of two or more distinct constituent materials into one. The individual components, on an atomic level, remain separate and distinct within the finished structure. The materials may have different physical or chemical properties, that when combined, produce a material with characteristics different from the individual components. A "dental composite" generally refers to a resin-based composite containing a mixture of a polymerizable resin and a filler, and is used in modern dentistry as a restorative material or an adhesive. Because of their aesthetic appeal and mechanical strength, dental composites are often considered superior to traditional silver-mercury amalgam and recently developed glass ionomer cement (GIC) restoratives.

In one or more embodiments, the polymerizable monomer in the currently disclosed dental composite comprises at least one selected from the group consisting of a methacrylate monomer, an acrylate monomer, an epoxy monomer, and a vinyl monomer.

As used herein, monomers are molecules which can undergo polymerization, thereby contributing constitutional repeating units to the structures of a macromolecule, a polymer, or a resin. The process by which monomers combine end to end to form a polymer is referred to herein as "polymerization". As used herein a "copolymer" refers to a polymer derived from more than one species of monomer and are obtained by "copolymerization" of more than one species of monomer. Copolymers obtained by copolymerization of two monomer and/or oligomer species may be termed bipolymers, those obtained from three monomers may be termed terpolymers and those obtained from four monomers may be termed quarterpolymers, etc. As used herein, "crosslinking", "cross-linking", "crosslinked", "cross-linked", a "crosslink", or a "cross-link" refers to polymers and resins containing branches that connect polymer chains via bonds that link one polymer chain to another. The crosslink may be an atom, a group of atoms, or a number of branch points connected by bonds, groups of atoms, or polymer chains. In a preferred embodiment, the polymerizable monomers in the current disclosure form crosslinking resins.

Polymerizable monomers used herein may include one or more mono-functional and/or multi-functional monomers. A mono-functional monomer refers to a monomer having one polymerizable group such as acrylate, methacrylate, epoxy, and vinyl present per molecule, while a multi-functional monomer refers to a monomer having two or more polymerizable groups present per molecule. Specifically, mono-functional methacrylate monomers useful in the present invention include, but are not limited to, methacrylic acid, methyl methacrylate (MMA), 2-hydroxyethyl methacrylate (HEMA) isopropyl methacrylate, n-propyl methacrylate, isopropyl methacrylate, n-butyl methacrylate, isobutyl methacrylate, hydroxyethyl methacrylate, hydroxypropyl methacrylate, hydroxybutyl methacrylate, propylene glycol monomethacrylate, isobomyl methacrylate, methoxyethoxyethyl methacrylate, ethoxyethoxyethyl methacrylate, tetrahydrofurfuryl methacrylate, acetoxyethyl methacrylate, phenoxyethylmethacrylate, methacryloyloxyethyl phthalate (MEP), and mixtures thereof. Useful multi-functional methacrylate monomers include, but are not limited to, bisphenol A-glycidyl methacrylate (bis-GMA), urethane dimethacrylate (UDMA), triethylene glycol dimethacrylate (TEGDMA), ethoxylated bisphenol A dimethacrylate (EB-PADMA), ethyleneglycol dimethacrylate, diethyleneglycol dimethacrylate, trimethyleneglycol dimethacrylate, glycerol dimethacrylate, trimethyolpropane trimethacrylate, tetraethyleneglycol dimethacrylate, 1,3-propanediol dimethacrylate, 1,4-butanediol dimethacrylate, 1,6-hexanediol dimethacrylate, 1,12-dodecanediol dimethacrylate, polyethyleneglycol dimethacrylate, trimethylolpropane trimethacrylate, 1,2,4-butanetriol trimethacrylate, pentaerythritol tetramethacrylate, diurethane dimethacrylate (DUDMA), pyromellitic acid glycerol dimethacrylate (PMGDM), and mixtures thereof.

Non-limiting examples of acrylate monomers include acrylic acid, methyl acrylate, ethyl acrylate, propyl acrylate, butyl acrylate, isobutyl acrylate, tort-butyl acrylate, pentyl acrylate, neopentyl acrylate, hexyl acrylate, cyclohexyl acrylate, heptyl acrylate, cyclohexylmethyl acrylate, octyl acrylate, 2-ethylhexyl acrylate, isooctyl acrylate, decyl acrylate, dodecyl acrylate, tetradecyl acrylate, hexadecyl acrylate, octadecyl acrylate, behenyl acrylate, ethyleneglycol diacrylate, neopentylglycol diacrylate, 1,6-hexanediol ethoxylate diacrylate, 1,3-butanediol diacrylate, 1,6-hexanediol diacrylate, 1,4-butanediol diacrylate, di(ethylene glycol) diacrylate, and mixtures thereof.

Epoxy monomers are compounds containing one or more glycidyl ether group, which include, but are not limited to, 1,2-epoxybutane, 1,2-epoxypentane, 1,2-epoxyhexane, glycidyl isopropyl ether, glycidyl 2,2,3,3-tetrafluoropropyl ether, butyl glycidyl ether, tert-butyl glycidyl ether, furfuryl glycidyl ether, 1,2-epoxyoctane, glycidyl 4-methoxyphenyl ether, 2-ethylhexyl glycidyl ether, (2,3-epoxypropyl)benzene, 1,2-epoxy-3-phenoxypropane, 1,2-epoxydodecane, neopentyl glycol diglycidyl ether, 1,4-cyclohexanedimethanol diglycidyl ether, 1,2,7,8-diepoxyoctane, 1,4-butanediol diglycidyl ether, resorcinol diglycidyl ether, N,N-diglycidyl-4-glycidyloxyaniline, and mixtures thereof.

Exemplary vinyl monomers include, but are not limited to, vinyl acetate, vinyl trifluoroacetate, vinyl propionate, vinyl valerate, vinyl neononanoate, vinyl decanoate, vinyl neodecanoate, vinyl stearate, vinyl benzoate, vinyl cinnamate, vinyl 4-tert-butylbenzoate, styrene, vinylbenzyl chloride, 4-vinylbenzoic acid, 2-(trifluoromethyl)styrene, 3-(trifluoromethyl)styrene, 4-(trifluoromethyl)styrene, 4-vinylanisole, 3-methylstyrene, 4-methylstyrene, fluorostyrene, 3-fluorostyrene, 4-fluorostyrene, 2,6-difluorostyrene, 2,3,4,5,6-pentafluorostyrene, 4-tert-butylstyrene, 2,4,6-trimethylstyrene, 3,4-dimethoxystyrene, 4-acetoxystyrene, divinylbenzene, 1,4-bis(4-vinylphenoxy)butane, 1,3,5-triallyl-1,3,5-triazine-2,4,6(1H,3H,5H)-trione, and mixtures thereof.

In some embodiments, the polymerizable monomer is one or more methacrylate monomers. In a preferred embodiment, the polymerizable monomer is one or more di-functional methacrylate monomer selected from the group consisting of bisphenol. A-glycidyl methacrylate (bis-GMA), urethane dimethacrylate (UDMA), triethylene glycol dimethacrylate (TEGDMA), and ethoxylated bisphenol A dimethacrylate (EBPADMA). In one embodiment, the polymerizable monomer is a combination of bis-GMA and TEGDMA at about 5:1 to about 1:5 mass ratio, about 4:1 to about 1:4 mass ratio, about 3:1 to about 1:3 mass ratio, about 2:1 to about 1:2 mass ratio, about 3:2 to about 2:3 mass ratio, or about 1:1 mass ratio. In another embodiment, the polymerizable monomer is a combination of UDMA and TEGDMA at about 5:1 to about 1:5 mass ratio, about 4:1 to about 1:4 mass ratio, about 3:1 to about 1:3 mass ratio, about 2:1 to about 1:2 mass ratio, about 3:2 to about 2:3 mass ratio, or about 1:1 mass ratio. In another embodiment, the polymerizable monomer is a combination of both mono-functional and multi-functional monomers. For example, the polymerizable monomer is a mixture of 2-hydroxyethyl methacrylate (HEMA) and bis-GMA at about 2:1 to about 1:10 mass ratio, about 1:1 to about 1:8 mass ratio, about 1:2 to about 1:6 mass ratio, or at about 1:3 to about 1:5 mass ratio. For another example, the polymerizable monomer is a mixture of tetrahydrofurfuryl methacrylate and bis-GMA at about at about 8:1 to about 1:2 mass ratio, about 6:1 to about 1:1 mass ratio, about 5:1 to about 2:1 mass ratio, or about 4:1 to about 3:1 mass ratio.

Fillers, when blended with the aforementioned polymerizable monomer, provide dental composites with greater mechanical strength and preferably with improved translucency. In one or more embodiments, the presently disclosed dental composite comprises a filler which is at least one selected from the group consisting of a glass filler, a ceramic filler, and a polymer-based filler. Useful glass fillers include, but are not limited to, silica, glasses that contain small amounts of heavy metals (barium, strontium, aluminum, etc) including barium borosilicate glass, aluminosilicate glass, boroaluminosilicate, strontium borosilicate glass, strontium-alumino-fluoro-silicate glass, and fluoroaluminosilicate glass, ytterbium trifluoride filler, and fiber glass filler. Exemplary ceramic fillers include, without limitation, zirconia filler, zirconia-silica filler, quartz filler, and porcelain filler. Polymer-based fillers include polymeric material that is pre-polymerized, e.g. poly(methyl methacrylate), poly(ethyl methacrylate), poly(acrylic acid), poly(methacryiic acid), poly(vinyl acetate), polyethylene, and polytetrafluoroethylene, and then ground into filler particles, and polymer fibers. In a preferred embodiment, the filler is at least one selected from the group consisting of silica, zirconia, and aluminosilicate.

Fillers that are commonly incorporated in a dental composite can be categorized into three major classes based on their average particle size, including macrofillers with an average particle size of 1-100 μm, microfillers with an average particle size of 0.01-0.1 μm, and nanofillers with an average particle size of 0.005-0.01 μm. In some embodiments, the filler used herein is a mixture of fillers with different average particle sizes, e.g. a mixture of microfiller and nanofillers at an approximate weight ratio of 1:1 to 10:1, 2:1 to 8:1, or 4:1 to 6:1. The particle size of the filler may be dependent on the identity of the filler. For example, in one embodiment where barium boroaluminosilicate glass particles are present as the filler, the medium particle diameter of the filler may range from about 0.1 to about 50 μm, from about 0.25 to about 25 μm, from about 0.5 to about 15 μm, or about 1.0 to about 7.5 μm. In another embodiment, where zirconia particles are served as the filler, the medium particle diameter of the filler may range from about 10 to about 500 nm, from about 20 to about 400 nm, from about 30 to about 300 nm, from about 40 to about 200 nm, from about 50 to about 100 nm, or from about 60 to about 80 nm.

Depending on the chemical structure of the filler, the filler used herein may be silanized to achieve better reinforcement by the resin matrix. Suitable means of silanization are generally known to those skilled in the art, and include treating a surface of the filler with a silanization agent. Typical silanization agents suitable for the purpose of the invention include, but are not limited to, silanes bearing a methacrylic functional group such as methacryloxypropyl trimethoxy silane; silanes bearing an epoxy group such as glycidoxy propyl trimethoxy silane or beta-(3,4-epoxycyclohexyl)ethyl trimethoxysilane; silanes comprising an amino functional group such as gamaaminopropyl trimethoxy silane, gama-aminopropyl triethoxy silane or N-beta(aminoethyl)gama-aminopropyl trimethoxy silane); and silanes comprising a mercapto group such as 3-mercaptopropyl trimethoxy silane.

In one or more embodiment, the filler is present in an amount of about 5 wt % to about 75 wt %, about 10 wt % to about 72 wt %, about 25 wt % to about 70 wt %, about 40 wt % to about 65 wt %, or about 50 wt % to about 60 wt % relative to the total weight of the dental composite. In certain embodiments, the filler is present in an amount of about 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, or 75 wt % relative to the total weight of the dental composite.

Polymerization initiators may be advantageously employed in a dental composite. Free-radical polymerization is a method of polymerization by which a polymer s cured by the successive addition of free-radical building blocks. A free radical initiator is capable of generating radical species, which can add on to monomer units and start radical polymerization process. A radical polymerization can be initiated by external energy such as heat, light, and/or electronic current. In one or more embodiment, the polymerization initiator present in the currently disclosed dental composite is a free radical initiator. In some embodiments, a free radical initiator is included in the polymerizable monomer liquid at a concentration in a range of about 0.01% to about 5.0%, about 0.1% to about 4.0%, about 0.5% to about 3.0%, or about 1.0% to about 2.0% by weight relative to the total weight of the polymerizable monomer. Exemplary free radical initiators include, but are not limited to, camphorquinone, benzil, benzophenone, acyl phosphine oxides, e.g. phenylbis(2,4,6-trimethylbenzoyl)phosphine oxide (Irgacure 819, BASF) and diphenyl(2,4,6-trimethylbenzoyl)phosphine oxide, azo compounds, e.g. azobisisobutyronitrile (AIBN), 1,1'-azobis(cyclohexanecarbonitrile) (ABCN), and 4,4'-azobis(4-cyanovaleric acid), and organic peroxides, e.g. benzoyl peroxide, lauroyl peroxide, methyl ethyl ketone peroxide (MEKP), tert-butyl hydroperoxide, and tert-butyl peroxybenzoate.

In some embodiments, a polymerization accelerator (co-initiator) that works in conjunction with the polymerization initiator to promote or improve the speed of polymerization reaction is added to the monomer liquid at a concentration in a range of about 0.1% to about 5.0% by weight relative to the total weight of the polymerizable monomer. Exemplary polymerization accelerators include, but are not limited to, N,N-dimethyl-p-toluidine, N,N-bis(2-hydroxyethyl)-p-toluidine, ethyl 4-(dimethylamino)benzoate, dimethylaminoethyl methacrylate, and N-(2-cyanoethyl)-N-methyl aniline.

In a preferred embodiment, a combination of free radical initiator camphorquinone and co-initiator ethyl 4-(dimethylamino)benzoate at a weight ratio of about 1:5 to about 2:1, about 1:4 to about 1:1, or about 1:3 to about 1:2, is employed as a polymerization initiator in the current invention.

In order to achieve adequate storage stability, especially for dental composites that are cured through a free-radical curing mechanism, it may be desirable to include a polymerization inhibitor to the polymerizable monomers at a concentration of about 0.001% to about 1.0%, about 0.01 to about 0.8%, about 0.05% to about 0.6%, about 0.1% to about 0.5%, or about 0.2% to about 0.4% by weight relative to the total weight of the polymerizable monomer. Small amounts of polymerization inhibitors can consume unwanted free radicals generated during manufacturing, transportation and storage stages, thus help avoid premature polymerization of dental composites. Examples of polymerization inhibitors include hydroquinone, 4-methoxyphenol, 2,6-di-tert-butyl-4-methylphenol (BHT) and the like.

In some embodiments, the polymerization initiator described herein can be activated by heat. In a preferred embodiment, the polymerization initiator described herein can be activated by an external light source. In a more preferred embodiment, the polymerization initiator can be activated by an external light source at a temperature of −20° C. to 100° C., preferably 0° C. to 80° C., preferably 10° C. to 60° C., or preferably 20° C. to 40° C., at a wavelength of 300-800 nm, 320-700 nm, 340-600 nm, 360-500 nm, or 380-400 nm. In a more preferred embodiment, the polymerization initiator can be activated by visible light, e.g. light at a wavelength between 380 nm to 700 nm.

Coconut oil, or copra oil, is an edible oil extracted from the kernel or meat of mature coconuts harvested from the coconut palm. Virgin coconut oil can be extracted through dry processing using dried copra or wet processing using raw coconut. Unlike virgin coconut oil, refined coconut oil is further heated, purified and deodorized and has no coconut taste or aroma. Refined coconut oil can be processed further into partially or fully hydrogenated coconut oil to increase its melting point. Because of its high saturated fat content, coconut oil has low tendency for oxidization, and is thus resistant to rancidification. In some embodiments where coconut oil is present, the currently disclosed dental composite comprises at least one selected from the list consisting of virgin coconut oil, refined coconut oil, and hydrogenated (or partially hydrogenated) coconut oil. In a preferred embodiment, the dental composite comprises refined coconut oil. Virgin coconut oil, refined coconut oil, and hydrogenated coconut oil used herein may be commercially available from a variety of vendors (e.g. Sigma Aldrich, VWR International, Acros Organics, and Avatar Corporation).

Coconut oil is used for home cooking, commercial food manufacturing, and cosmetic, industrial, and pharmaceutical purposes. Coconut oil differs from other oils because of its high content of medium chain fatty acids, including saturated fatty acids e.g. caproic acid (C6:0), caprylic acid (C8:0), capric acid (C10:0), and lauric acid (C12:0), other saturated myristic acid (C14:0) and palmitic acid (C16:0), and monounsaturated oleic acid (C18:1). The concentration of each fatty acids found in coconut oil is listed in Table 1 (G. C. Gervajio, 2005, Fatty acids and derivatives from coconut oil, Bailey's industrial oil and fat products, $6^{th}$ edition, Edited by F. Shahidi, John Wiley & Sons, Inc.—incorporated herein by reference in its entirety). In embodiments where the derivative of coconut oil is present, the dental composite described herein comprises at least one fatty acid selected from the group consisting of lauric acid, caprylic acid, capric acid, myristic acid, oleic acid, esters thereof, and salts thereof.

The esters of fatty acids derived from coconut oil, e.g. lauric acid, caprylic acid, capric acid, myristic acid, and oleic acid, can be obtained by esterification and further transesterification of the fatty acid with a mono-functionalized alcohol or a polyol. Non-limiting examples of useful alcohols include methanol, ethanol, isopropanol, butanol, pentanol, menthol, ethylene glycol, propylene glycol, glycerol, trimethylol propane, erythritol, pentaerythritol, xylitol, sorbitol, and mixtures thereof.

The salts of fatty acids of coconut oil, e.g. lauric acid, caprylic acid, capric acid, myristic acid, and oleic acid can be synthesized from the parent fatty acid that contains an acidic moiety by conventional chemical methods, e.g. reacting the free acid moiety with a stoichiometric amount of the appropriate base in water or in an organic solvent, or in a mixture of the two; generally non-aqueous media like ether, ethyl acetate, ethanol, isopropanol, or acetonitrile are preferred. Suitable salts include those derived from metals such as sodium and potassium, lithium, calcium, magnesium, barium, iron, copper, silver and zinc, as well as those salts with a non-metal cation, e.g. an ammonium cation and a phosphonium cation. Non-limiting examples of non-metal cations include ammonium, monoalkylammonium, dialkylammonium, trialkylammonium, tetraalkylammonium, monoarylammonium, diarylammonium, triarylammonium, tetraarylammonium, and tetraarylphosphonium cations.

In one or more embodiments, the dental composite described herein comprises a mixture of coconut oil and at least one fatty acid selected from the group consisting of lauric acid, caprylic acid, capric acid, myristic acid, oleic acid, esters thereof, and salts thereof at a weight ratio of 100:1 to 1:100, 75:1 to 1:75, 50:1 to 1:50, 25:1 to 1:25, 10:1 to 1:10, 5:1 to 1:5, or 2:1 to 1:2, wherein the mixture is present in an amount ranging from about 0.1 wt % to about 20 wt %, from about 1 wt % to about 15 wt %, from about 5 wt % to about 12.5 wt %, or from about 8 wt % to about 10 wt % relative to the total weight of the dental composite.

In at least one embodiment, the dental composite disclosed herein consists essentially of (i) the polymerizable monomer, (ii) the filler in an amount of 40-75 wt %, (iii) the polymerization initiator, and (iv) coconut oil in an amount ranging from about 0.1 wt % to about 20 wt %, from about 1 wt % to about 15 wt %, from about 5 wt % to about 12.5 wt %, or from about 8 wt % to about 10 wt %, wherein the weight percentages are based on a total weight of the dental composite.

TABLE 1

Percentage by weight of fatty acids in coconut oil relative to the total weight of coconut oil

| Fatty acid | Formula | Weight (%) |
|---|---|---|
| Caproic | $C_6H_{12}O_2$ | 0.2-0.8 |
| Caprylic | $C_8H_{16}O_2$ | 6-9 |
| Capric | $C_{10}H_{20}O_2$ | 6-10 |
| Lauric | $C_{12}H_{24}O_2$ | 46-50 |
| Myristic | $C_{14}H_{28}O_2$ | 17-19 |
| Palmitic | $C_{16}H_{32}O_2$ | 8-10 |
| Oleic | $C_{18}H_{34}O_2$ | 5-7 |
| Stearic | $C_{18}H_{36}O_2$ | 2-3 |
| Linoleic | $C_{18}H_{32}O_2$ | 1-2.5 |

As a major component in coconut oil, lauric acid is known for its antibacterial and anti-inflammatory effect (Alimentarius C C (2016). JOINT FAO/WHO FOOD STANDARDS PROGRAMME In: CA COMMISSION editor. Rome, Italy: CX-STAN, pp. 210; Butt U, ElShaer A, Snyder L A, Chaideinenou A, Alany R G (2016). Fatty acid microemulsion for the treatment of neonatal conjunctivitis: quantification, characterisation and evaluation of antimicrobial activity. *Drug delivery and translational research* 6(6):722-734; and Umerska A, Cassisa V, Matougui N, Joly-Guillou M L, Eveillard M, Saulnier P (2016). Antibacterial action of lipid nanocapsules containing fatty acids or monoglycerides as co-surfactants. *European journal of pharmaceutics and biopharmaceutics: official journal of Arbeitsgemeinschaft fur Pharmazeutische Verfahrenstechnik eV* 108:100-110, each incorporated herein by reference in their entirety). In a preferred embodiment, the derivative of coconut oil incorporated in the dental composite comprises lauric acid, an ester thereof, or a salt thereof.

In some embodiments, the dental composite disclosed herein consists essentially of (i) the polymerizable monomer, (ii) the filler in an amount of 40-75 wt %, (iii) the polymerization initiator, and (iv) one or more derivatives of coconut oil in an amount ranging from about 0.1 wt % to about 20 wt %, from about 1 wt % to about 15 wt %, from about 5 wt % to about 12.5 wt %, or from about 8 wt % to about 10 wt %, wherein the derivatives of coconut oil are selected from the group consisting of lauric acid, caprylic acid, capric acid, myristic acid, oleic acid, esters thereof, and salts thereof, and wherein the weight percentages are based on a total weight of the dental composite. In a preferred embodiment, the dental composite disclosed herein consists essentially of (i) the polymerizable monomer, (ii) the filler in an amount of 40-75 wt %, (iii) the polymerization initiator, and (iv) lauric acid, an ester thereof, or a salt thereof present in an amount ranging from about 0.1 wt % to about 20 wt %, from about 1 wt % to about 15 wt %, from about 5 wt % to about 12.5 wt %, or from about 8 wt % to about 10 wt %, wherein the weight percentages are based on a total weight of the dental composite.

In one embodiment of the invention, derivatives of coconut oil further include a chemical derivative formed by subjecting the coconut oil or a derivative of coconut oil such as lauric acid to a chemical reaction. It is preferred that this chemical reaction, alternately referred to herein as derivatization or functionalization, alters the hydrophobicity and/or lipophilicity of the coconut oil, the derivative of coconut oil or preferably lauric acid. Such chemical modification can take place by subjecting coconut oil, a derivative of coconut oil such as lauric acid, or other extracted or a fraction of coconut oil to a chemical reaction with one or more oxidants. In a preferred embodiment, the oxidant is a peroxide selected from the group consisting of inorganic peroxides, e.g. hydrogen peroxide, sodium peroxide, and barium peroxide, and organic peroxides, e.g. tertbutyl hydroperoxide, cumene hydroperoxide, dicumyl peroxide, tertbutyl peroxide, and tertbutyl peroxybenzoate. The chemical reaction of coconut oil or a derivative of coconut oil such as lauric acid with a peroxide, e.g. hydrogen peroxide fortes a chemical derivative that has an increased content of oxygen. The oxygen content is associated with the addition of one or more functional groups such as a hydroxyl group, an ether group, a carbonyl group, an ester group, a peroxy group, an oxirane group, a glycidyl group, an epoxy group, and the like to one or more fatty acid chains present in the coconut oil or the chain of fatty acids such as lauric acid. In a preferred embodiment, after a modification or functionalization of the coconut oil or the derivative of coconut oil by the chemical reaction with reagents such as a peroxide, the resulting chemical derivative has a compositional shift in which the amount of oxygen is increased, based on the total weight of all of the components in the chemical derivative, by about 5%, preferably about 3%, 2%, 1% or about 0.5% compared to the total contribution of oxygen in the coconut oil, based on the total weight of coconut oil, or compared to the total content of oxygen in the derivative of coconut oil, based on the total weight of the derivative of coconut oil. The compositional shift of oxygen content may be monitored by various analytical techniques including elemental analysis (e.g. combustion analysis, X-ray photoelectron spectroscopy (XPS)), mass spectrometry, Fourier-transform infrared (FT-IR) spectroscopy, and nuclear magnetic resonance (NMR) spectroscopy. In some embodiments, where the derivative of coconut oil is present, the dental composite described herein comprises at least one aforementioned chemical derivative.

In one or more embodiments, the dental composite described herein comprises a mixture of coconut oil and at least one aforementioned chemical derivative at a weight ratio of 100:1 to 1:100, 75:1 to 1:75, 50:1 to 1:50, 25:1 to 1:25, 10:1 to 1:10, 5:1 to 1:5, or 2:1 to 1:2, wherein the mixture is present in an amount ranging from about 0.1 wt % to about 20 wt %, from about 1 wt % to about 15 wt %, from about 5 wt % to about 12.5 wt %, or from about 8 wt % to about 10 wt % relative to the total weight of the dental composite.

In some embodiments, the dental composite disclosed herein consists essentially of (i) the polymerizable monomer, (ii) the filler in an amount of 40-75 wt %, (iii) the polymerization initiator, and (iv) one or more aforementioned chemical derivatives in an amount ranging from 0.1 wt % to 20 wt %, from about 1 wt % to about 15 wt %, from about 5 wt % to about 12.5 wt %, or from about 8 wt % to about 10 wt % wherein the weight percentages are based on a total weight of the dental composite.

Chemical functionalization of coconut oil provides several important advantages to the presently disclosed dental composites. The chemical derivative obtained by modifying the hydrophobic and/or lipophilic characteristics of the coconut oil or the derivative of coconut oil may have a different rate of diffusion from the dental composites relative to the coconut oil or the derivative of coconut oil prior modification or functionalization, e.g., prior to the chemical reaction. In one aspect of the invention, wherein the coconut oil and/or the derivative of coconut oil is not chemically bonded to the dental composite, diffusion of the coconut oil from the dental composite provides one means of antimicrobial activity whereby the coconut oil derivatives leaves the dental composite and functions to inhibit or "kill" bacteria on a surface of the dental composites. For example, the chemical derivative functionalized with hydrophilic groups (e.g. hydroxyls and carboxyls) may have a faster rate of diffusion by at least 5%, at least 10%, at least 15%, at least 20%, at least 30%, at least 40%, or at least 50% relative to the rate of diffusion of the unmodified coconut oil or the derivative of coconut oil from the dental restoratives. Alternatively, the chemical derivative functionalized with hydrophobic groups (e.g. esters) may have a different rate of diffusion by at least 5%, at least 10%, at least 15%, at least 20%, at least 30%, at least 40%, or at least 50% relative to the rate of diffusion of unmodified coconut oil or the derivative of coconut oil from the dental restoratives.

In another aspect of the invention, the functional groups of the chemical derivative, such as modified coconut oil and/or the derivative of coconut oil, may permit chemical bonding between the chemical derivative and the dental composite. In this aspect of the invention portions of coconut oil, such as functionalized "tails" of the fatty acid may be exposed or near the surface of a dental restorative made from the dental composite. The exposure of these groups on the surface affects the biophilicity/biophobicity characteristics of the dental composite and thereby discourages the growth of microbial films. For example, the surface of the dental restorative made from the dental composite comprising the chemical derivative with hydrophobic groups may have lower wettability, which can be characterized by an increased surface contact angle with water by at least 2°, at least 4°, at least 6°, at least 8°, or at least 10° relative to the surface contact angle with water of unmodified coconut oil or the derivative of coconut oil. Alternately, the exposure of these groups on the surface of the dental composite exerts a destructive force on bacterial cells coming into contact with the dental restorative.

In addition to coconut oil, derivatives of coconut oil, and/or aforementioned chemical derivatives, the dental composite may further include a second antimicrobial agent, e.g. triclosan, chlorhexidine, cetyl pyridinium chloride, benzethonium chloride, bromochlorophene, and quaternary ammonium salts such as benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldithethylammonium chloride, undecylenic acid, fluconazole, amphotericin B, sphingosine, and nystatin. In some embodiments, the additional antimicrobial agent may be an enzyme that has biofilm inhibiting or biofilm disrupting activity, e.g. dextranase and other glycoside hydrolases. The second antimicrobial agent may be included in an amount of 0.1-2 wt %, 0.2-1.5 wt %, 0.4-1.0 wt %, or 0.5-0.8 wt % relative to the total weight of the dental composite.

The dental composite of the current disclosure may further include a fluoride source selected from sodium fluoride, potassium fluoride, aluminum fluoride, zinc fluoride, stannous fluoride, ammonium fluoride, sodium monofluorophosphate and the like. The fluoride source may present in an amount of 0.01-2 wt %, 0.05-1 wt %, 0.1-0.5 wt %, or 0.2-0.4 wt % relative to the total weight of the dental composite.

In certain embodiments, the dental composite described herein may further include a pigment, primarily for aesthetic reasons. Suitable pigments and dyes include, but are not limited to, titanium dioxide, zinc oxide, lake pigments and the like. The pigment is preferably pre-grinded into one of the components of the dental composite, since it is unlikely to function well if added as a separate powder. The pigment may present in 0.01-1 wt %, preferably 0.1-0.8 wt %, preferably 0.2-0.6 wt %, preferably 0.3-0.5 wt % relative to the total weight of the dental composite.

Methods of preparing dental composites are generally known to those skilled in the art. For example, the dental composite disclosed herein may be prepared by (i) mixing polymerizable monomers (e.g. BisGMA, TEGDMA, and UDMA) at aforementioned weight ratio to form a monomer liquid, (ii) adding photoinitiators and co-initiators (e.g. CQ and EDBA) to the monomer liquid to form a polymerizable resin at aforementioned weight ratio and amount, (iii) adding fillers (e.g. silica, aluminosilicates, and/or zirconia), and coconut oil and/or derivatives of coconut to the polymerizable resin at the aforementioned weight ratio to form a composite mixture, (v) mixing the composite mixture by agitating for 0.1-12 hours, 0.5-6 hours, or 1-3 hours to form the dental composite. In a preferred embodiment, the dental composite is prepared at a temperature of 5° C. to 40° C., 10° C. to 30° C., 15° C. to 28° C., or at around 25° C.

Methods of agitating a mixture include, without limitation, using an agitator, a vortexer, a rotary shaker, a magnetic stirrer, a centrifugal mixer, a dual asymmetric centrifugal mixer, or an overhead stirrer. In one embodiment, the composite mixture is agitated by sonication in an ultrasonic bath or with an ultrasonic probe. In another embodiment, the mixture is left to stand without being stirred. In another embodiment, the mixture is agitated using a magnetic stirrer with a rotational speed of at least 250 rpm, preferably at least 500 rpm, more preferably at least 750 rpm. In a preferred embodiment, the composite mixture is mixed with a spatula. In another preferred embodiment, the mixture is mixed using a dual asymmetric centrifugal mixer, e.g. SpeedMixer (FlackTek Inc.) at a speed of at least 800 rpm, preferably at least 1000 rpm, more preferably at least 1500 rpm.

According to a second aspect, the present disclosure relates to a dental restoration, comprising a cured dental composite of the first aspect. Curing conditions and procedures are generally known to those skilled in the art. In some embodiments, wherein the polymerization initiator can be activated by an external light source, the currently disclosed dental composite may be cured by applying light at a proper wavelength and with sufficient intensity to the dental composite to initiate and propagate polymerization. In one or more embodiments, light is applied to the dental composite during curing for a period of time of at least 10 seconds, at least 20 seconds, at least 30 seconds, at least 40 seconds, at least 1 minute, at least 2 minutes, or at least 5 minutes. Depending on the identity of the photo-initiator, a light source at a wavelength of 300-800 nm, 320-700 nm, 340-600 nm, 360-500 nm, 380-480 nm, or 400-450 nm may be applied. Depending on the composition of the dental composite, the curing may be performed at a light intensity of about 200-2000 mW/cm$^2$, about 400-1500 mW/cm$^2$, about 600-1200 mW/cm$^2$, or about 800-1000 mW/cm$^2$. Applicable light sources for the curing described herein may be commercially available from a variety of vendors, including, but not limited to, Elipar™ S10 LED Curing Light (3M ESPE), XL3000 (3M ESPE), PROLITE (Dentsply Sirona), SPECTRUM (Dentsply Sirona), VIVALUX II (Ivoclar-Vivadent), and OPTII UX 500 (Demetron-Kerr).

A degree of conversion in a dental composite may be determined after curing. The degree of conversion (% DC) can be calculated by comparing the ratio of the aliphatic carbon-carbon double bond (C=C) relative to an internal standard, e.g. an aromatic or alkyl component for the cured and uncured dental composites (Karabela M M, Sideridou I D (2011). Synthesis and study of properties of dental resin composites with different nanosilica particles size. *Dental materials: official publication of the Academy of Dental Materials* 27(8):825-835, incorporated herein by reference in its entirety). Useful analytical tools for determining % DC include Fourier-transform infrared (FT-IR) spectroscopy, near-infrared (NIR) spectroscopy, Raman spectroscopy, and nuclear magnetic resonance (NMR) spectroscopy. For example, DC % of the cured dental restorative described herein may be measured using a FT-IR. spectrometer (e.g. Spectrum One, Perkin-Elmer). FT-IR spectra within a proper region (e.g. 600-4000 cm$^{-1}$) may be acquired with a proper acquisition resolution (e.g. 2 cm$^{-1}$, 4 cm$^{-1}$, 8 cm$^{-1}$, 16 cm$^{-1}$, or 32 cm$^{-1}$) and number of scans (e.g. 4, 8, 16, 32, or 64) per spectrum before and after curing. In some embodiments, wherein the polymerizable monomer comprises bis-GMA, DC % of the dental restorative may be calculated as: DC %=100×{1−[(A1637/A1608)$_{after\ curing}$/(A1637/A1608)$_{before\ curring}$]}, wherein A1637 and A1608 represent FT-IR peak height of aliphatic C=C bond at 1637 cm$^{-1}$ and aromatic C=C at 1608 cm$^{-1}$, and "before curing" and "after curing" designate FT-IR spectra collected for dental composite before and after curing. In a preferred embodiment, the dental restorative formed by a cured dental composite of the present disclosure in any of its embodiments has a DC % in the range of 30%-90%, preferably 35%-80%, preferably 40% to 70%, preferably 45% to 60%.

As used herein, flexural strength, also known as modulus of rupture, or bend strength, or transverse rupture strength is a material property, defined as the stress in a material just before it yields in a flexure test. The flexural strength represents the highest stress experienced within the material at its moment of yield. The transverse bending test is most frequently employed, in which a specimen having either a circular or rectangular cross section is bent until fracture or yielding using a three point flexural test (three point bending test) technique. Procedures for the three point bending test are generally known to those skilled in the art, and are described in, e.g. Tavassoli Hojati S, Alagheinand H, Hamze F, Ahmadian Babaki F, Rajab-Nia R, Rezvani M B el al. (2013). Antibacterial, physical and mechanical properties of flowable resin composites containing zinc oxide nanoparticles. *Dental materials: official publication of the Academy of Dental Materials* 29(5):495-505; ISO 178, Plastics-Determination of flexural properties; and ISO 4049:2000(E), Dentistry-Polymer-based filling, restorative and luting materials, each incorporated herein by reference in their entirety. In some embodiments, a three-point bending test is performed on the currently disclosed dental restorative using a universal testing machine e.g. Instron 8871 (Instron), AGS-X (Shimadzu), and eXpert 7600 (ADMET), at a crosshead speed of 0.01 mm/min to 100 mm/min, 0.05 mm/min to 10 mm/min, 0.1 mm/min to 1 mm/min, or about 0.5 mm/min. In a preferred embodiment, the dental restorative formed by a cured dental composite of the present disclosure in any of its embodiments has a flexural strength of about 50 to about 140 MPa, preferably about 55 to about 130 MPa, preferably about 60 to about 120 MPa, preferably about 65 to about 110 MPa, preferably about 70 to about 100 MPa, preferably about 75 to about 90 MPa.

Hardness is a measure of how resistant solid matter is to various kinds of permanent shape change when a compressive force is applied. Indentation hardness tests are used in mechanical engineering to determine the hardness of a material to deformation. Several indentation hardness testing methods including Rockwell, Brinell, and Vickers methods exist, wherein the examined material is indented until an impression is formed. In some embodiments, a Vickers hardness test is performed on the currently disclosed dental restorative using a diamond indenter, e.g. MicroMet 6040 microhardness testing machine (Buehler), MS-ZH Microhardness Testing System (Newage), and Micro Vickers Hardness Tester HMV-G (Shimadzu). Procedures for the Vickers hardness test are generally known to those skilled in the art, and are described in, e.g. Monterubbianesi R, Orsini G, Tosi G, Conti C, Librando V, Procaccini M et al. (2016). Spectroscopic and Mechanical Properties of a New Generation of Bulk Fill Composites. *Frontiers in physiology* 7:652; and ASTM E384: Standard Test Method for Knoop and Vickers Hardness of Materials, each incorporated herein by reference in their entirety. In a preferred embodiment, the dental restorative formed by a cured dental composite of the present disclosure in any of its embodiments has a Vickers hardness number HV of about 50 to about 100, preferably about 55 to about 95, preferably about 60 to about 90, preferably about 65 to about 85, preferably about 70 to about 80.

As used herein, "microorganism" or "microbe" refers to in particular fungi, and gram-positive and gram-negative bacteria.

Exemplary pathogenic fungi include classes of ascomycota, basidomycota, deuteromycota and zygomycota, particularly human pathogenic forms of candida, which is one of the most common causes of fungal infections worldwide. Exemplary pathogenic *candida* (abbreviated to C. in the following) species include, but are not limited to *C. albicans, C. auris, C. glabrata, C. tropicalis, C. parapsilosis, C, krusei, C. guilliermondii, C. lusitaniae, C. kefyr, C. farnata, C. inconspicua, C. rugosa, C. duhliniensis, C. parapsilosis, C. norvegensis, C. orthoparapsilosis*, and *C. stellatoidea*.

Notable oral bacteria include, but are not limited to *Propionibacterium acnes, Stapylococcus aureus, Streptococcus pyogenes, Corynebacterium tenuis, Corynebacterium diphtheriae, Corynebacterium minutissirnum, Micrococcus sedentarius, Bacillus anthracia, Neisseria meningitides, Neisseria gonorrhoeae, Pseudomonas aeruginosa, Pseudomonas pseudomallei, Borrelia burgdorferi,*

*Treponema pallidum, Mycobacterium tuberculosis, Escherichia coli, Streptococcus gordonii, Streptococcus mutans, Streptococcus salivarius, Actinomyces naeslundii, Salmonella* species, *Nitrosomonas* species, *Aquabacterium* species, *Stenotrophomonas* species, *Xanthomonas* species, *Haemophilus* species, as well as all microorganisms that are described by Paster et al. (Paster B J, Boches S K, Galvin J L, Ericson R E, Lau C N, Levanos V A, Sahasrabudhe A, Dewhirst F E. Bacterial diversity in human subgingival plaque. *J. Bacteriol.* 2001, 12, 3770-3783, incorporated herein by reference in its entirety).

According to a third aspect, the present disclosure relates a method of preventing or reducing growth of a microorganism in an oral cavity, the method comprising applying the dental restoration of the second aspect to the oral cavity of a subject in need thereof. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

In one or more embodiments, the aforementioned method can prevent or reduce growth of a microorganism which is at least one selected from the group consisting of *Streptococcus mutans* and *Streptococcus sobrinus*. Pathogenic oral bacteria such as *Streptococcus mutans, Streptococcus sobrinus, Streptococcus sanguinis* and *Streptococcus salivarius* are associated with oral diseases including tooth caries, dental cavities, periodontal diseases, gingivitis, pericoronitis, and endodontitis. Dental caries is triggered by demineralization of teeth due to acids generated by oral bacteria. Cariogenic bacteria such as gram-positive *Streptococcus mutans* are considered as a primary cause for tooth decays and dental cavities as they can metabolize carbohydrates, e.g. glucose, fructose, and lactose to organic acids, e.g. lactic acid. The increasing acidic condition in an oral cavity can etch tooth enamel and accelerate the rate of teeth demineralization.

As used herein, exemplary dental restoratives include, but are not limited to, fillings, inlays, onlays, veneers, temporary and permanent crowns and bridges, implants, and orthodontic devices such as brackets and arch-wires. In a preferred embodiment, the dental restorative described herein is employed as a filling to restore a surface of a tooth from which a decayed portion has been removed.

In some embodiments, the dental restorative of the current disclosure may provide a concentration of coconut oil and/or a derivative of coconut oil described herein in a medium such as water, culture broth, e.g. Brain Heart Infusion (BHI) broth and. Todd Hewitt Broth, and saliva. In certain embodiments, the dental restorative of the current disclosure may provide a concentration of coconut oil and/or a derivative of coconut oil described herein less than the solubility limit of coconut oil and/or the derivative of coconut oil in a medium such as water, culture broth, and saliva. It is recognized that solubility limit of a compound may be different in different media. As used herein, the term "provide a concentration" of coconut oil and/or a derivative of coconut oil refers to a property of the dental restorative to release or transfer to a medium such as water, culture broth, and saliva, resulting in a concentration of coconut oil and/or the derivative of coconut oil in the medium. In some embodiments, the dental restorative may provide a concentration of coconut oil and/or a derivative of coconut up to about 1.0 mol, up to about 0.5 mol, up to about 0.4 mol, up to about 0.3 mol, up to about 0.2 mol, up to about 0.1 mol, up to about 0.05 mol, up to about 0.01 mol, up to about 5 mmol, up to about 1 mmol, up to about 0.5 mmol, up to about 0.1 mmol, up to about 0.05 mmol, up to about 0.01 mmol in a medium. In certain embodiments, the dental restorative may provide a concentration of coconut oil and/or a derivative of coconut oil up to about the solubility limit of coconut oil and/or the derivative of coconut oil in a medium. In one or more embodiments, the dental restorative provide a concentration of coconut oil and/or a derivative of coconut oil that is sufficient to prevent or reduce growth of a microorganism in the oral cavity of a subject.

In a preferred embodiment, a concentration of coconut oil and/or a derivative of coconut oil in a medium can be analyzed using a high-performance liquid chromatography (HPLC) (Marigo L, Spagnuolo G, Malara F, Martorana G E, Cordaro M, Lupi A et al. (2015). Relation between conversion degree and cytotoxicity of a flowable bulk-fill and three conventional flowable resin-composites. *European review for medical and pharmacological sciences* 19(23):4469-4480; and Tokay U, Koyuturk A E, Aksoy A, Ozmen B (2015). Do the monomers release from the composite resins after artificial aging? *Microscopy research and technique* 78(4):255-259, each incorporated herein by reference in their entirety), e.g. Waters 2695 (Waters Corporation), Agilent 1260 Infinity HPLC (Agilent Technologies), and Ulti-Mate 3000 HPLC (Thermo Scientific).

The dental restorative applied to the oral cavity of a subject may be in contact with a surface in the oral cavity for a time sufficient to prevent or reduce growth of a microorganism in the oral cavity. The time may be up to about 1 second, up to about 10 seconds, up to about 30 seconds, up to about 1 minute, up to about 2 minutes, up to about 5 minutes, up to about 10 minutes, up to about 15 minutes, up to about 30 minutes, up to about 60 minutes, up to about 2 hours, up to about 4 hours, up to about 6 hours, up to about 8 hours, up to about 10 hours, or up to about 12 hours. The time may be less than about 1 month, less than about 3 weeks, less than about 2 weeks, less than about 1 week, less than about 4 days, less than about 2 days, less than about 1 day, less than about 20 hours, less than about 18 hours, less than about 16 hours, or less than about 14 hours.

In some embodiments, preventing or reducing growth of a microorganism in an oral cavity is evaluated by measuring a microbial count (Miki S, Kitagawa H, Kitagawa R, Kiba W, Hayashi M, Imazato S (2016). Antibacterial activity of resin composites containing surface pre-reacted glass-ionomer (S-PRG) filler, *Dental materials: official publication of the Academy of Dental Materials* 32(9):1095-1102, incorporated herein by reference in its entirety). Preferably, the number of viable microorganisms is counted using a slide count method and/or a direct culture method (plate count).

The "slide count" method utilizes a microscope slide in a chamber that is especially designed to enable cell counting. A total number of cells in a sample can be determined by looking at the sample under a microscope and counting the number manually. A number of viable cells can also be determined using the slide count method if a viability dye is added to the sample. Exemplary viability dyes include, but are not limited to, Trypan Blue, Calcein-AM, Erythrosine B, propidium iodide, and 7-aminoactinomycin D.

"Colony-forming unit (CFU)" refers to a unit used to estimate the number of viable bacteria or fungal cells in a sample. The purpose of direct culture method (plate count) is to estimate the number of cells present based on their ability to give rise to colonies under specific conditions of nutrient medium, temperature and time. Theoretically, one viable cell can give rise to a colony through replication. A sample solution of microbes at an unknown concentration is often serially diluted in order to obtain at least one plate with a countable number of CFUs. Counting colonies is performed manually using a pen and a click-counter, or automatically using an automated system and a software tool for counting CFUs. In a preferred embodiment, preventing or reducing growth of a microorganism in an oral cavity is evaluated by the plate count method.

Preventing or reducing growth of a microorganism in an oral cavity may be understood to indicate a reduction of the number of microorganism cells in the oral cavity. In some embodiments, the number of microorganisms in the oral cavity characterized by a microbial count is reduced by at least 10%, preferably at least 20%, more preferably at least 30%, more preferably at least 40%, more preferably at least 45%, more preferably at least 50%, more preferably at least 55%, more preferably at least 60%, more preferably at least 65%, more preferably at least 70%, more preferably at least 80%, more preferably at least 90%, or more preferably at least 95%, with respect to use of an untreated control dental restorative, e.g. a dental restorative comprising no coconut oil or derivatives of coconut oil described herein, in an oral cavity. Ideally, the growth of microorganisms in the oral cavity may be completely or almost completely prevented.

As used herein, the term "biofilm" refers to a matrix comprising bacteria. The biofilm matrix is often composed of extracellular polymeric substances including extracellular polysaccharides, proteins, and DNA. Compared to planktonic bacteria, bacteria in biofilms are often able to survive and thrive in harsher environmental conditions as they are surrounded by a dense and protected matrix structure. Consequently, bacteria in a biofilm show a higher resistance towards antibiotics than planktonic bacteria. Biofilms are present as dental plaque when formed on a surface in an oral cavity. Dental plaque is responsible for dental caries, gingivitis, and periodontal diseases. In restorative dentistry, secondary caries often occur at the interface between the restoration and the tooth cavity due to bacteria colonization, and biofilm/plaque formation. Furthermore, dental resin restoratives in general do not prevent secondary caries as no biofilm inhibition mechanism is imbedded in them.

According to a forth aspect, the present disclosure relates a method of inhibiting formation of a biofilm on a surface in an oral cavity, the method comprising applying the dental restoration of the second aspect to a surface in the oral cavity of a subject in need thereof.

In one or more embodiments, the surface in the oral cavity is a hard surface including, without limitation, bone, dental enamel, dentin, and dental restorations. In a preferred embodiment, the surface in the oral cavity comprises a tooth.

Pathogenic bacteria *Streptococcus mutans* and *Streptococcus sobrinus* are major contributors to dental biofilm formation and growth as they are capable of producing polysaccharides from sucrose. These sticky polysaccharides enable the bacteria to aggregate with one another and adhere to tooth enamel to form biofilms and dental plaques. In one or more embodiments, the aforementioned method can inhibit formation or growth of the biofilm comprising at least one selected from the group consisting of *Streptococcus mutans* and *Streptococcus sobrinus*. In a preferred embodiment, the aforementioned method can be further used to reduce the occurrence of secondary caries at an interface between the dental restoration described herein and the tooth cavity.

In one or more embodiments, the formation of a biofilm can be evaluated by measuring a two-dimensional (2D) and/or three-dimensional (3D) structure of the biofilm, e.g. height, length, and width using 2D visualization tools such as light microscopy, scanning electron microscopy (SEM), and transmission electron microscopy (TEM), and 3D visualization tools such as confocal laser scanning microscopy. Additionally, the viability of a biofilm may be quantified as a number of viable microbes in a biofilm measured by the aforementioned microbial count methods or a metabolic assay.

In a preferred embodiment, the formation of a biofilm is analyzed by measuring a thickness of the biofilm. In some embodiments, the thickness of biofilm in the oral cavity characterized by a 2D or 3D visualization tool is reduced by at least 10%, preferably at least 20%, more preferably at least 30%, more preferably at least 40%, more preferably at least 45%, more preferably at least 50%, more preferably at least 55%, more preferably at least 60%, more preferably at least 65%, more preferably at least 70%, more preferably at least 80%, more preferably at least 90%, or more preferably at least 95%, with respect to use of an untreated control dental restorative, e.g. a dental restorative comprising no coconut oil or derivatives of coconut oil described herein, in an oral cavity. Ideally, the formation of biofilms in the oral cavity may be completely or almost completely inhibited.

In another embodiment, the foination of a biofilm is evaluated by measuring a number of viable microbes in the biofilm. In some embodiments, the number of viable microbes in the biofilm in the oral cavity characterized by a slide count method using a viability dye is reduced by at least 10%, preferably at least 20%, more preferably at least 30%, more preferably at least 40%, more preferably at least 45%, more preferably at least 50%, more preferably at least 55%, more preferably at least 60%, more preferably at least 65%, more preferably at least 70%, more preferably at least 80%, more preferably at least 90%, or more preferably at least 95%, with respect to use of an untreated control dental restorative, e.g. a dental restorative comprising no coconut oil or derivatives of coconut oil described herein, in an oral cavity.

Thus, the foregoing discussion discloses and describes merely exemplary embodiments of the present disclosure. As will be understood by those skilled in the art, the present disclosure may be embodied in other specific forms without departing from the spirit or essential characteristics thereof. Accordingly, the disclosure of the present invention is intended to be illustrative, but not limiting the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A dental composite, comprising:
   a polymerizable monomer;
   a filler in an amount of 40-75 wt % based on a total weight of the dental composite;
   a polymerization initiator; and
   a chemical derivative of a coconut oil in an amount ranging from 0.1 wt % to 20 wt % based on the total weight of the dental composite, wherein the chemical derivative of coconut oil is a reaction product of coconut oil and hydrogen peroxide and has an oxygen content that is greater by 0.5-5 wt % in comparison to the coconut oil before reacting with hydrogen peroxide.

2. The dental composite of claim 1, consisting essentially of:
   the polymerizable monomer;
   the filler in an amount of 40-75 wt %;

the polymerization initiator; and the chemical derivative of the coconut oil in an amount ranging from 0.1 wt % to 20 wt %;

wherein the weight percentages are based on a total weight of the dental composite.

3. The dental composite of claim 1, wherein the polymerizable monomer is at least one selected from the group consisting of a methacrylate monomer, an acrylate monomer, an epoxy monomer, and a vinyl monomer.

4. The dental composite of claim 3, wherein the polymerizable monomer is a methacrylate monomer.

5. The dental composite of claim 4, wherein the methacrylate monomer is at least one selected from the group consisting of bisphenol A-glycidyl methacrylate (bis-GMA), urethane dimethacrylate (UDMA), triethylene glycol dimethacrylate (TEGDMA), ethoxylated bisphenol A dimethacrylate (EBPADMA), and 2-hydroxyethyl methacrylate (HEMA).

6. The dental composite of claim 1, wherein the filler is at least one selected from the group consisting of a glass filler, a ceramic filler, and a polymer-based filler.

7. The dental composite of claim 1, wherein the filler is at least one selected from the group consisting of silica, zirconia, and aluminosilicate.

8. The dental composite of claim 1, wherein the polymerization initiator is a free radical initiator.

9. The dental composite of claim 8, wherein the free radical initiator is at least one selected from the group consisting of camphorquinone, an acyl phosphine oxide, an azo compound, and an organic peroxide.

10. A dental restoration, comprising a cured dental composite of claim 1.

11. The dental restoration of claim 10, which has a flexural strength of about 70 MPa to about 150 MPa.

12. The dental restoration of claim 10, which has a Vickers hardness number HV of about 60 to about 100.

13. The dental restoration of claim 10, comprising the filler in an amount of 65-75 wt %.

* * * * *